United States Patent [19]

Sasaki et al.

[11] Patent Number: 4,721,792
[45] Date of Patent: Jan. 26, 1988

[54] N,N',N'',N'''-TETRAKIS(SUBSTITUTED BENZYL)-ACETYLENECARBAMIDE DERIVATIVES

[75] Inventors: Manji Sasaki, Ibaraki; Chinehito Ebina, Minoo; Haruki Okamura, Osaka; Shinichi Yachigo, Toyonaka; Tamaki Ishii, Suita, all of Japan

[73] Assignee: Sumitomo Chemical Company, Limited, Osaka, Japan

[21] Appl. No.: 825,559

[22] Filed: Jan. 30, 1986

[30] Foreign Application Priority Data

Feb. 13, 1985 [JP] Japan .................................. 60-27325

[51] Int. Cl.$^4$ ........................................... C07D 235/00
[52] U.S. Cl. ....................................... 548/304; 524/91
[58] Field of Search .......................... 548/304; 524/91

[56] References Cited

U.S. PATENT DOCUMENTS

| 4,448,915 | 5/1984 | Terada et al. | 524/93 |
| 4,507,417 | 3/1985 | Ishii et al. | 524/101 |
| 4,511,491 | 4/1985 | Ishii et al. | 252/404 |

FOREIGN PATENT DOCUMENTS 219345  12/1984  Japan .................................. 524/108

Primary Examiner—Alan L. Rotman
Assistant Examiner—Kurt G. Briscoe
Attorney, Agent, or Firm—Wenderoth, Lind & Ponack

[57] ABSTRACT

There are provided acetylenecarbamide derivatives of the formula:

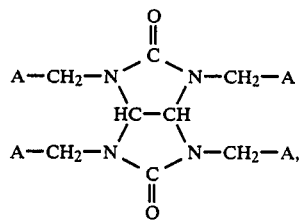

wherein A represents

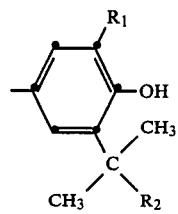

in which $R_1$ represents a hydrogen atom or a $C_1$–$C_4$ alkyl group, and $R_2$ represents a $C_2$–$C_9$ alkyl group. These derivatives are useful as stabilizers for polymeric organic substances susceptible to thermal and oxygen-induced degradation.

2 Claims, No Drawings

N,N',N'',N'''-TETRAKIS(SUBSTITUTED BENZYL)-ACETYLENECARBAMIDE DERIVATIVES

The present invention relates to an acetylenecarbamide derivative represented by the general formula (I),

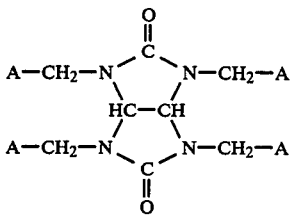

wherein A represents

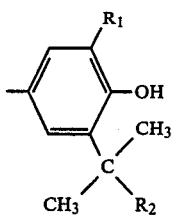

in which $R_1$ represents a hydrogen atom or a $C_1$-$C_4$ alkyl group, and $R_2$ represents a $C_2$-$C_9$ alkyl group, its production and a stabilizer for organic substances containing it as an effective ingredient.

Various kinds of organic substances such as polyolefins (e.g. polyethylene, polypropylene), styrene type synthetic resins (e.g. polystyrene, impact-resistant polystyrene, ABS), engineering plastics (e.g. polyacetal, polyamide), polyurethane, etc. find wide application in many fields. It is however well known that when these organic substances are used alone, their stability becomes a problem, for example they deteriorate by the action of heat, light and oxygen on processing or use, thereby showing a remarkable reduction in mechanical properties accompanied by phenomena such as softening, embrittlement, surface cracking, discoloration and the like.

It is also well known that, in order to solve such problem, various kinds of phenolic type, phosphite type or sulfur-containing antioxidant are added or used in the course of production and processing of high polymers. For example, it is well known that phenolic type antioxidant such as 2,6-di-tert-butyl-4-methylphenol, 2,2'-methylenebis(4-methyl-6-tert-butylphenol), 4,4'-butylidenebis(3-methyl-6-tert-butylphenol), n-octadecyl 3-(3,5-di-tert-butyl-4-hydroxyphenyl)propionate, 1,1,3-tris(2-methyl-4-hydroxy-5-tert-butylphenyl)btuane, pentaerythritol tetrakis [3-(3,5-di-tert-butyl-4-hydroxyphenyl)propionate], the ester of terephthalic acid with 3-(3,5-di-tert-butyl-4-hydroxyphenyl)-propanol and the like are used alone, or these phenolic type antioxidants are used in combination with phosphite type antioxidants such as tris(nonylphenyl)-phosphite, distearyl pentaerythritol diphosphite and the like, or sulfur-containing antioxidants such as dilauryl thiodipropionate, dimyristyl thiodipropionate, distearyl thiodipropionate and the like.

But, these methods are not yet quite satisfactory in terms of thermal and oxidation stability, thermal discoloration resistance, sublimation resistance and the like.

Also, a stabilizer comprising pentaerythritol tetrakis [3-(3,5-dialkyl-4-hydroxphenyl)propionate] and pentaerythritol tetrakis (3-alkylthiopropionate) is proposed in Japanese Patent Kokai (Laid-open) No. 20337/1984. This stabilizer is fairly superior to the conventional ones, but it is not always quite safisfactory in terms of thermal and oxidation stability, thermal discoloration resistance, etc. so that the appearance of stabilizers of higher performance has been demanded.

The present inventors extensively studied to solve these problems, and as a result, found that a particular acetylenecarbamide derivative represented by the general formula (I), even when used alone, will give to the organic substance higher thermal and oxidation stability than does the above well-known stabilizer, and besides that, when it is used together with a particular sulfur-containing compound, it will give excellent thermal and oxidation stability which can never be forecast from the conventional antioxidant-combination techniques. The present inventors thus completed the present invention.

The acetylenecarbamide derivative of the present invention represented by the general formula (I) can be produced by reacting acetylenecarbamide with a compound represented by the general formula (III),

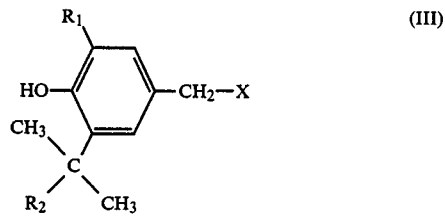

wherein $R_1$ and $R_2$ have the same meanings as described above, and X represents a hydroxyl or $C_1$-$C_4$ alkoxy group or a dialkyldithiocarbamoyloxy group of the following formula,

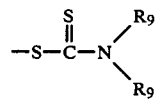

in which $R_9$ represents a $C_1$-$C_4$ alkyl group, or by simultaneously reacting acetylenecarbamide with formaldehyde and a phenol represented by the general formula (IV),

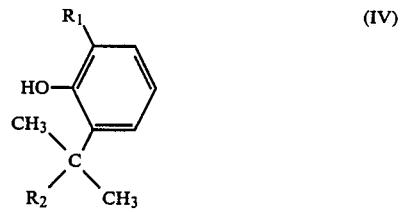

wherein $R_1$ and $R_2$ have the same meanings as described above.

In that case, references may be made to the methods disclosed in Japanese Patent Kokai (Laid-open) Nos. 67690/1983, 21686/1984, 27891/1984, 27892/1984 and 29688/1984 and the like.

In the general formula (I) representing the acetylenecarbamide derivative, a substituent $R_1$ includes a hydrogen atom or a methyl, ethyl, propyl, isopropyl, butyl, isobutyl, sec-butyl and tert-butyl groups, etc., and a substituent $R_2$ includes an ethyl, propyl, isopropyl, butyl, sec-butyl, tert-butyl, 2,2-dimethylpropyl, pentyl, hexyl, heptyl, octyl, nonyl and 2,2,4,4-tetramethylpentyl groups, etc.

Typical examples of such compound will be shown in Table 1. These compounds are unknown to the literature, and the present inventors were the first to synthesize and isolate them.

TABLE 1

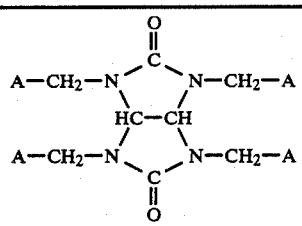

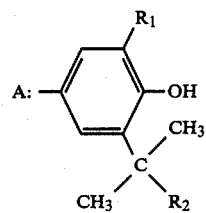

| Compound No. | $R_1$ | $R_2$ |
|---|---|---|
| I-1 | —CH₃ | —CH₂—C(CH₃)₂—CH₃ (—CH₂—C(CH₃)(CH₃)—CH₃) |
| I-2 | —H | Same as above. |
| I-3 | —CH₂CH₃ | Same as above. |
| I-4 | —C(CH₃)₂—CH₃ | Same as above. |
| I-5 | —CH₃ | —CH(CH₃)₂ |
| I-6 | —CH₃ | —CH₂—C(CH₃)₂—CH₂—C(CH₃)₂—CH₃ |

In using the present acetylenecarbamide derivative as a stabilizer for organic substances, its amount is generally 0.01 to 5 parts by weight, preferably 0.05 to 1 part by weight based on 100 parts by weight of the organic substance.

For blending the derivative (I) with organic substances, the well-known apparatus and methods for incorporating stabilizers, pigments, fillers, etc. in organic substances may be used almost as such.

In using the stabilizer for organic substances of the present invention, other additives such as antioxidants of thioether type, phosphite type or phenolic type other than that described in the present invention, ultraviolet absorbers, light stabilizers, metal deactivators, metal soaps, nucleating agents, lubricants, antistatic agents, flame retardants, pigments, fillers and the like may be used together.

Particularly, a further more improvement in the thermal and oxidation stability can be attained by using a thioether compound together. Such thioether compound includes for example dialkyl thiodipropionates (e.g., dilauryl thiodipropionate, dimyristyl thiodipropionate, distearyl thiodipropionate) and thioether compounds represented by the general formulae (II-1) and (II-2):

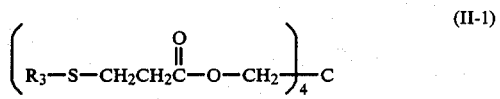

wherein $R_3$ represents a $C_4$-$C_{20}$ alkyl group, and

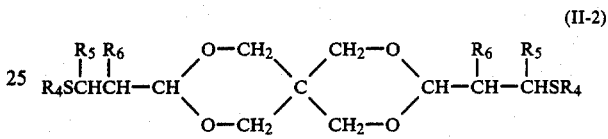

wherein $R_4$ represents a $C_3$-$C_{18}$ alkyl group, and $R_5$ and $R_6$ independently represent a hydrogen atom or a $C_1$-$C_6$ alkyl group. The mixing ratio (by weight) of the acetylenecarbamide derivative (I) to the thioether compound (II) is generally 1 to 0.5–15, preferably 1 to 1–10, more preferably 1 to 2–6.

Particularly, when at least one member selected from the thioether compounds represented by the general formulae (II-1) and (II-2) is used together, excellent effect can be obtained which can never be forecast from the well-known techniques to combine phenolic type compounds with thioether compounds, so that the use of these thioether compounds is particularly preferred.

In the general formula (II-1), a substituent $R_3$ is most preferably a $C_6$-$C_{18}$ alkyl group in terms of the thermal and oxidation stability.

Typical examples of such compound will be shown in Table 2.

TABLE 2

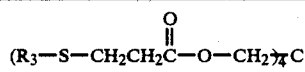

| Compound No. | $R_3$ |
|---|---|
| II-1-1 | —C₆H₁₃ |
| II-1-2 | —C₁₂H₂₅ |
| II-1-3 | —C₁₈H₃₇ |

In the general formula (II-2), it is preferred in terms of the thermal and oxidation stability that a substituent $R_4$ is a $C_{12}$-$C_{18}$ alkyl group, and substituents $R_5$ and $R_6$ are independently a hydrogen atom or a $C_1$-$C_3$ alkyl group.

Typical examples of such compound will be shown in Table 3.

TABLE 3

$$R_4SCHCH-CH \begin{matrix} R_5 & R_6 \\ | & | \end{matrix} \diagdown_{O-CH_2}^{O-CH_2} \diagup C \diagdown_{CH_2-O}^{CH_2-O} \diagup CH-CHCHSR_4 \begin{matrix} R_6 & R_5 \\ | & | \end{matrix}$$

| Compound No. | R₄ | R₅ | R₆ |
|---|---|---|---|
| II-2-1 | —C₈H₁₇ | —CH₃ | —H |
| II-2-2 | —C₁₂H₂₅ | —C₄H₉ | —H |
| II-2-3 | —C₁₂H₂₅ | —CH₃ | —H |
| II-2-4 | —C₁₈H₃₇ | —CH₃ | —H |
| II-2-5 | —C₁₂H₂₅ | —H | —H |
| II-2-6 | —C₁₈H₃₇ | —H | —CH₃ |

When the acetylenecarbamide derivative (I) and thioether compound (II) are added in mixture to organic substances, the amount of the mixture is generally 0.01 to 5 parts by weight, preferably 0.05 to 1 part by weight based on 100 parts by weight of the organic substance. But, the derivative (I) and the compound (II) may separately be incorporated in the organic substance without being mixed in advance.

The light fastness of the organic substances can be improved by using a light stabilizer therewith. As the light stabilizer, there are mentioned for example benzophenone compounds such as 2-hydroxy-4-methoxybenzophenone, 2-hydroxy-4-n-octoxybenzophenone, 2,2'-dihydroxy-4,4'-dimethoxybenzophenone, etc.; benzotriazole compounds such as 2-(2-hydroxy-5-methylphenyl)benzotriazole, 2-(2-hydroxy-3-tert-butyl-5-methylphenyl)-5-chlorobenzotriazole, 2-(2-hydroxy-3,5-di-tert-butylphenyl)benzotriazole, 2-(2-hydroxy-3,5-di-tert-butylphenyl)-5-chlorobenzotriazole, 2-(2-hydroxy-3,5-di-tert-amylphenyl)benzotriazole, 2-(2-hydroxy-5-tert-octylphenyl)benzotriazole, 2-[2-hydroxy-3,5-bis(α,α-dimethylbenzyl)phenyl]benzotriazole, etc.; benzoate compounds such as phenyl salicylate, p-tert-butylphenyl salicylate, 2,4-di-tert-butylphenyl 3,5-di-tert-butyl-4-hydroxybenzoate, hexadecyl 3,5-di-tert-butyl-4-hydroxybenzoate, etc.; nickel compounds such as Ni salt of N,N-dibutyldithiocarbamic acid, [2,2'-thiobis(4-tert-octylphenolate)]-butylamine nickel complex, Ni salt of (3,5-di-tert-butyl-4-hydroxybenzyl)phosphonic acid monoethyl ester, etc.; hindered piperidine compounds such as 2,2,6,6-tetramethyl-4-piperidyl benzoate, bis(2,2,6,6-tetramethyl-4-piperidyl)sebacate, bis(2,2,6,6-tetramethyl-4-piperidyl) 2-(3,5-di-tert-butyl-4-hydroxybenzyl)-2-n-butylmalonate, 1-[2-{3-(3,5-di-tert-butyl-4-hydroxyphenyl)propionyloxy}ethyl]-4-[3-(3,5-di-tert-butyl-4-hydroxyphenyl)propionyloxy]-2,2,6,6-tetramethylpiperidine, a condensation product of dimethyl succinate with 1-(2-hydroxyethyl)-4-hydroxy-2,2,6,6-tetramethylpiperidine, a reaction product of dihaloalkylene with N,N'-bis(2,2,6,6-tetramethylpiperidyl)alkylenediamine, a reaction product of 2,6-dichloro-1,3,5-triazine with N,N'-bis(2,2,6,6-tetramethylpiperidyl)alkylenediamine, etc.; acrylonitrile compounds such as ethyl α-cyano-β,β-diphenylacrylate, methyl α-cyano-β-methyl-β-(p-methoxyphenyl)acrylate, etc.; and oxalic acid diamide compounds such as N-2-ethylphenyl-N'-2-ethoxy-5-tert-butylphenyloxalic acid diamine, N-2-ethylphenyl-N'-2-ethoxyphenyloxalic acid diamide, etc.

Also, the color of the organic substances can be improved by using a phosphite type antioxidant therewith. Such antioxidant includes for example tris(nonylphenyl)phosphite, distearyl pentaerythritol diphosphite, tris(2,4-di-tert-butylphenyl)phosphite, tris(2-tert-butyl-4-methylphenyl)phosphite, bis(2,4-di-tert-butylphenyl)-pentaerythritol diphosphite, tetrakis(2,4-di-tert-butylphenyl) 4,4'-biphenylene diphosphite and the like.

Thus, by using the acetylenecarbamide derivative of the present invention, the stability of organic substances is markedly improved. As such organic substances, there are mentioned for example low-density polyethylene, high-density polyethylene, linear low-density polyethylene, chlorinated polyethylene, EVA resin, polypropylene, polyvinyl chloride, methacrylic resin, polystyrene, impact-resistant polystyrene, ABS resin, AES resin, MBS resin, polyethylene terephthalate, polybutylene terephthalate, polyamide, polyimide, polycarbonate, polyacetal, polyurethane, unsaturated polyester resin, besides, rubbers such as natural rubber, isoprene rubber, butadiene rubber, acrylonitrile/butadiene copolymer rubber, styrene/butadiene copolymer rubber, etc.; and blends of these resins. Of these resins, polypropylene is particularly effective.

The present invention will be illustrated in detail with reference to the following examples, but it is not limited to these examples.

Of the test compounds in the examples, the compounds AO-1 to AO-8 are ones shown in Table 4, and the compounds other than these are ones shown in Tables 1 to 3.

A symbol  in Table 4 means

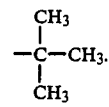

TABLE 4

| Test Compound | Structure |
|---|---|
| AO-1 | 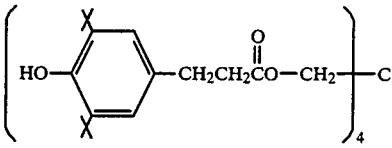 |
| AO-2 | 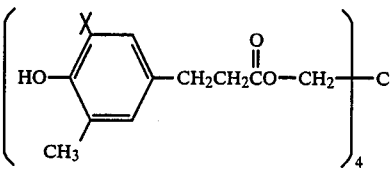 |
| AO-3 | 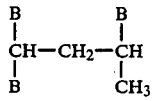 |

$$B = \ \ $$ 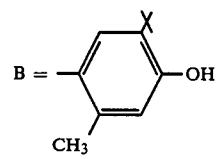

TABLE 4-continued

| Test Compound | Structure |
|---|---|
| AO-4 | (structure shown: tetrakis D-CH2 groups on bicyclic diurea core with D = 4-hydroxyphenyl with X substituents) |
| AO-5 | (structure shown: tetrakis E-CH2 groups on bicyclic diurea core with E = 4-hydroxy-3-methylphenyl with X substituent) |
| AO-6 | (HO-phenyl-CH3 with X substituents) |
| AO-7 | $S{-}[CH_2CH_2COC_{12}H_{25}]_2$ (with C=O) |
| AO-8 | $S{-}[CH_2CH_2COC_{18}H_{37}]_2$ (with C=O) |

EXAMPLE 1

(Production example for the compound No. I-1)

To a mixture comprising 30.0 g (0.114 mole) of 4-hydroxy-3-methyl-5-(1,1,3,3-tetramethylbutyl)benzyl methyl ether, 3.36 g (0.0236 mole) of acetylenecarbamide and 25 ml of sulfolane was added 4.4 g of a methanol solution containing 28 wt.% of sodium methoxide (corresponding to 0.023 mole) under a nitrogen atmosphere. The mixture was heated, and reaction was carried out for 20 hours during which generated methanol was distilled off. After completion of the reaction, the reaction mixture was diluted with toluene and chloroform and neutralized with aqueous dilute hydrochloric acid. The oily layer was salted out and dried, and the solvent was removed by evaporation. The residue was recrystallized from toluene to obtain 17.7 g of a white crystalline N,N′,N″,N‴-tetrakis[4-hydroxy-3-methyl-5-(1,1,3,3-tetramethylbutyl)benzyl]acetylenecarbamide.

Yield, 70%.
Melting point, 159°–161° C.
Mass analysis (FD-mass), 1071 (M+1)+
Elementary analysis:

|  | C (%) | H (%) | N (%) |
|---|---|---|---|
| Found | 76.27 | 9.40 | 5.13 |
| Calculated | 76.22 | 9.59 | 5.23 |

EXAMPLES 2 to 6

(Production examples for the compounds Nos. I-2 to I-6)

Using the corresponding benzyl methyl ethers, reaction and after-treatment were carried out in the same manner as in Example 1, and column chromatography on silica gel was then applied to obtain the compounds I-2 to I-6. The physical properties and the results of mass analysis (FD-mass) and elementary analysis of every compound are shown in Table 5.

TABLE 5

| Compound No. | Property | Mass analysis | Elementary analysis (%)* | | |
|---|---|---|---|---|---|
| | | | C | H | N |
| I-2 | Glassy | 1015 | 75.92 (75.70) | 9.21 (9.33) | 5.47 (5.52) |
| I-3 | Glassy | 1127 | 76.81 (76.69) | 9.63 (9.83) | 4.89 (4.97) |
| I-4 | Glassy | 1239 | 77.68 (77.50) | 10.02 (10.24) | 4.39 (4.52) |
| I-5 | Glassy | 959 | 75.23 (75.12) | 8.98 (9.04) | 5.75 (5.84) |
| I-6 | Glassy | 1295 | 78.05 (77.85) | 10.19 (10.42) | 4.18 (4.32) |

*Values in parentheses are calculated values.

EXAMPLE 7

The blend described below was mixed on a mixer for 5 minutes and then melt-kneaded at 180° C. on a mixing roll to obtain a compound. This compound was formed into a sheet of 1 mm in thickness on a hot press kept at 210° C., and test pieces of 40×40×1 mm (thick) were prepared therefrom. This test piece was placed in a Geer oven kept at 150° C. and measured for a period of time required for 30% of its area to become brittle. This period of time was taken as a thermal embrittlement induction period and used for evaluation of the thermal and oxidation stability. The result is shown in Table 6.

Compounding:

|  | Part by weight |
|---|---|
| Unstabilized polypropylene resin | 100 |
| Calcium stearate | 0.1 |
| Test compound | 0.15 |

TABLE 6

| | No. | Test compound | Thermal embrittlement induction period (hour) |
|---|---|---|---|
| Present example | 1 | I-1 | 980 |
| | 2 | I-2 | 950 |
| | 3 | I-3 | 1000 |
| | 4 | I-4 | 1050 |
| | 5 | I-5 | 970 |
| | 6 | I-6 | 990 |
| Comparative example | 7 | AO-4 | 820 |
| | 8 | No addition | 20 or less |

EXAMPLE 8

The blend described below was mixed on a mixer for 5 minutes and then melt-kneaded at 180° C. on a mixing roll to obtain a compound. This compound was formed into a sheet of 1 mm in thickness on a hot press kept at 210° C., and test pieces of 40×40×1 mm (thick) were prepared therefrom. This test piece was placed in a Geer oven kept at 160° C. and measured for a period of time required for 30% of its area to become brittle. This period of time was taken as a thermal embrittlement induction period and used for evaluation of the thermal and oxidation stability. The result is shown in Table 7.

Compounding:

| | Part by weight |
|---|---|
| Unstabilized polypropylene resin | 100 |
| Calcium stearate | 0.1 |
| Test compound | variable |

TABLE 7

| | | Phenolic type antioxidant | | Sulfur-containing antioxidant | | Thermal embrittlement induction period (hour) |
|---|---|---|---|---|---|---|
| | No. | Kind | Part by weight | Kind | Part by weight | |
| Present example | 1 | I-1 | 0.05 | II-1-1 | 0.2 | 1620 |
| | 2 | " | " | II-1-2 | 0.1 | 1440 |
| | 3 | " | " | " | 0.2 | 1820 |
| | 4 | " | " | " | 0.3 | 2260 |
| | 5 | " | " | II-1-3 | 0.2 | 1640 |
| | 6 | " | " | II-2-1 | " | 1630 |
| | 7 | " | " | II-2-2 | " | 1660 |
| | 8 | " | " | II-2-3 | " | 1770 |
| | 9 | " | " | II-2-4 | " | 1820 |
| | 10 | " | " | II-2-5 | " | 1780 |
| | 11 | " | " | II-2-6 | " | 1790 |
| | 12 | I-2 | " | II-1-2 | " | 1810 |
| | 13 | " | " | II-2-4 | " | 1800 |
| | 14 | " | " | II-2-5 | " | 1770 |
| | 15 | I-3 | " | II-1-2 | " | 1810 |
| | 16 | " | " | II-2-4 | " | 1800 |
| | 17 | " | " | II-2-5 | " | 1780 |
| | 18 | I-5 | " | II-1-2 | " | 1800 |
| | 19 | " | " | II-2-4 | " | 1790 |
| | 20 | " | " | II-2-5 | " | 1780 |
| | 21 | I-6 | " | II-1-2 | " | 1810 |
| | 22 | " | " | II-2-4 | " | 1790 |
| | 23 | " | " | II-2-5 | " | 1780 |
| Comparative example | 24 | AO-1 | " | II-1-2 | " | 400 |
| | 25 | " | " | II-2-4 | " | 440 |
| | 26 | " | " | II-2-5 | " | 430 |
| | 27 | " | " | AO-7 | " | 450 |
| | 28 | " | " | AO-8 | " | 750 |
| | 29 | AO-2 | " | II-1-2 | " | 1600 |
| | 30 | " | " | II-2-4 | " | 1580 |
| | 31 | " | " | AO-8 | " | 620 |
| | 32 | AO-3 | " | II-1-2 | " | 400 |
| | 33 | " | " | II-2-4 | " | 420 |
| | 34 | " | " | AO-8 | " | 650 |
| | 35 | AO-4 | " | II-1-2 | " | 410 |
| | 36 | " | " | II-2-4 | " | 450 |
| | 37 | " | " | AO-8 | " | 770 |
| | 38 | AO-5 | " | II-1-2 | " | 1420 |
| | 39 | " | " | II-2-4 | " | 1400 |
| | 40 | " | " | AO-8 | " | 750 |
| | 41 | — | — | — | — | 5 |

EXAMPLE 9

The test compound in Table 8 was bead-peptized together with an anionic surface active agent to prepare a suspension, and a prescribed amount, as shown in Table 8, of the suspension was added to a graft ABS latex. The mixture was as usual salted out with an aqueous magnesium sulfate solution, filtered, washed with water and dried to obtain an ABS resin powder which is a test sample. The thermal and oxidation stability of this ABS resin power was evaluated by the methods described below. The result is shown in Table 8.

1. The degree of discoloration of the ABS resin powder after thermal ageing on a 180° C. Geer oven was observed.
2. The oxygen absorption induction period (I.P.) in a 170° C. oxygen atmosphere was measured using an oxygen absorption induction period measurement apparatus.
3. The ABS resin powder was repeatedly extruded on a small extruder (screw: D=20 mmφ, L/D=25; strand die: D=3 mmφ, L/D=10) under the following condition. The degree of discoloration of the ABS pellet after 4th extrusion was evaluated by a color difference, ΔYI, between said ABS pellet and the antioxidant-free ABS pellet after 1st extrusion.

Extrusion condition:
Number of revolution: 40 rpm

| Temperature: | $C_1$ | $C_2$ | $C_3$ | D |
|---|---|---|---|---|
| | 220° C. | 240° C. | 260° C. | 280° C. |

4. The ABS pellet after 4th extrusion obtained by the method in 3 above was compression-molded under a condition of 180° C.×10 min. to prepare the test piece No. 1 specified by JIS K 7111. Thereafter, the Charpy impact test was carried out according to JIS K 7111 using a Charpy impact tester.

TABLE 8

| | | Present example | | | | | Comparative example | | | | |
|---|---|---|---|---|---|---|---|---|---|---|---|
| | | No. | | | | | | | | | |
| | | 1 | 2 | 3 | 4 | 5 | 6 | 7 | 8 | 9 | 10 | 11 |
| Phenolic type antioxidant | I-1 | 0.5 | 0.5 | 0.5 | | | | | | | | |
| | I-6 | | | | 0.5 | 0.5 | 0.5 | | | | | |
| | AO-1 | | | | | | | 0.5 | 0.5 | 0.5 | 0.5 | |

TABLE 8-continued

| | | 12 | 13 | 14 | 15 | 16 | 17 | 18 | 19 |
|---|---|---|---|---|---|---|---|---|---|
| | AO-4 | | | | | | | | 0.5 |
| | AO-6 | | | | | | | | |
| Sulfur-containing antioxidant | II-1-2 | 0.5 | | | 0.5 | | | 0.5 | 0.5 |
| | II-2-4 | | 0.5 | | | 0.5 | | 0.5 | |
| | II-2-5 | | | 0.5 | | | 0.5 | | |
| | AO-8 | | | | | | | 0.5 | |
| Degree of discoloration | After 30 minutes | Pale yellow | " | " | " | " | " | Yellowish brown | " | " | " | " |
| | After 60 minutes | Yellowish brown | " | " | " | " | " | Brown | " | " | " | " |
| I.P. (minute) | | 205 | 200 | 205 | 200 | 195 | 200 | 145 | 145 | 145 | 145 | 145 |
| ΔYI | | 11.2 | 11.5 | 11.3 | 11.3 | 11.6 | 11.3 | 14.5 | 14.3 | 14.5 | 14.6 | 14.6 |
| Value of Charpy impact test (Kgf · cm/cm) | | 20.5 | 20.3 | 20.5 | 20.2 | 19.8 | 20.0 | 11.7 | 11.6 | 11.6 | 11.4 | 11.6 |

| | | Comparative example No. | | | | | | | |
|---|---|---|---|---|---|---|---|---|---|
| | | 12 | 13 | 14 | 15 | 16 | 17 | 18 | 19 |
| Phenolic type antioxidant | I-1 | | | | | | | | No. addition |
| | I-6 | | | | | | | | |
| | AO-1 | | | | | | | | |
| | AO-4 | 0.5 | 0.5 | 0.5 | | | | | |
| | AO-6 | | | | 0.5 | 0.5 | 0.5 | 0.5 | |
| Sulfur-containing antioxidant | II-1-2 | | | | 0.5 | | | | |
| | II-2-4 | 0.5 | | | | 0.5 | | | |
| | II-2-5 | | 0.5 | | | | 0.5 | | |
| | AO-8 | | | 0.5 | | | | 0.5 | |
| Degree of discoloration | After 30 minutes | " | " | " | Deep brown | Deep brown | " | " | " |
| | After 60 minutes | " | " | " | Blackish brown | Blackish brown | " | " | " |
| I.P. (minute) | | 145 | 145 | 145 | 150 | 150 | 150 | 140 | 10 |
| ΔYI | | 14.4 | 14.6 | 14.8 | 14.5 | 14.6 | 14.8 | 15.0 | 15.9 |
| Value of Charpy impact test (Kgf · cm/cm) | | 11.4 | 11.4 | 11.3 | 12.4 | 12.5 | 12.4 | 11.7 | 7.2 |

Note:
The amount added is the weight of the test compound per 100 parts by weight of the solid matter of the resin.

What is claimed is:

1. An acetylenecarbamide derivative represented by the formula (I),

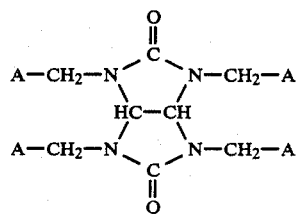

wherein A represents

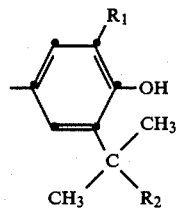

in which $R_1$ represents a hydrogen atom or a $C_1$-$C_4$ alkyl group, and $R_2$ represents a $C_3$-$C_9$ alkyl group.

2. N,N',N'',N'''-tetrakis[4-hydroxy-3-methyl-5-(1,1,3,3-tetramethylbutyl)benzyl]acetylenecarbamide.

* * * * *